(12) United States Patent
Lui et al.

(10) Patent No.: US 8,586,756 B2
(45) Date of Patent: Nov. 19, 2013

(54) PROCESS FOR THE PREPARATION OF 2,2-DIFLUOROETHYLAMINE DERIVATIVES STARTING FROM N-(2,2-DIFLUOROETHYL)PROP-2-EN-1-AMINE

(75) Inventors: Norbert Lui, Odenthal (DE); Jens-Dietmar Heinrich, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 148 days.

(21) Appl. No.: 13/292,930

(22) Filed: Nov. 9, 2011

(65) Prior Publication Data
US 2012/0123130 A1    May 17, 2012

Related U.S. Application Data

(60) Provisional application No. 61/413,008, filed on Nov. 12, 2010.

(30) Foreign Application Priority Data

Nov. 12, 2010   (EP) .................................... 10191066

(51) Int. Cl.
*C07D 213/38*    (2006.01)

(52) U.S. Cl.
USPC ....................................................... 546/329

(58) Field of Classification Search
USPC ....................................................... 546/329
See application file for complete search history.

(56) References Cited

U.S. PATENT DOCUMENTS

| | | | |
|---|---|---|---|
| 8,084,452 B2 * | 12/2011 | Jeschke et al. | 514/247 |
| 2009/0253749 A1 | 10/2009 | Jeschke et al. | |
| 2010/0222593 A1 | 9/2010 | Lui et al. | |
| 2010/0274021 A1 | 10/2010 | Lui et al. | |

FOREIGN PATENT DOCUMENTS

| | | |
|---|---|---|
| WO | 2007115644 | 10/2007 |
| WO | 2009036900 | 3/2009 |
| WO | 2009036901 | 3/2009 |
| WO | 2010105747 | 9/2010 |

OTHER PUBLICATIONS

Salvatore, RN "Synthesis of Secondary Amines" Tetrahedron 2001, 57, 7785-7811.*

Extended European Search Report of EP 10191066.9 dated Apr. 20, 2011 (5 pages).
Escoubet et al., "Methods for the Cleavage of Allylic and Propargylic C—N Bonds in Amines and Amides—Selected Alternative Applications of the 1,3-Hydrogen Shift", Eur. J. Org. Chem. 2005, pp. 3855-3873.
International Search Report (German version with English translation) and Written Opinion (German version) based on PCT/EP2011/069625 mailed Dec. 5, 2011.

* cited by examiner

*Primary Examiner* — David K O Dell
(74) *Attorney, Agent, or Firm* — Miles & Stockbridge P.C.

(57) ABSTRACT

Process for the preparation of 2,2-difluoroethylamine derivatives of the formula (IV)

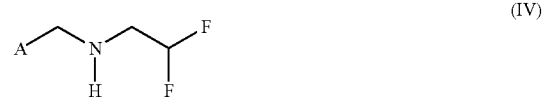

comprising the steps (i) and (ii):
step (i): reaction of N-(2,2-difluoroethyl)prop-2-en-1-amine of the formula (I)

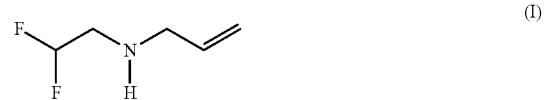

with a compound of the formula (II)

A-CH$_2$-E    (II)

to give a compound of the formula (III)

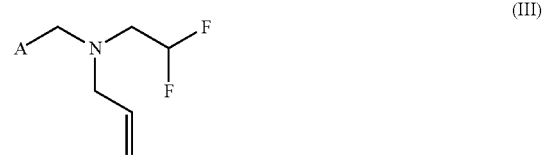

optionally in the presence of an inorganic or organic base, and step (ii): removal of the allyl group from the compound of the formula (III), in which, in the formulae (II), (III) and (IV), A and E have the meanings given in the description.

20 Claims, No Drawings

PROCESS FOR THE PREPARATION OF 2,2-DIFLUOROETHYLAMINE DERIVATIVES STARTING FROM N-(2,2-DIFLUOROETHYL)PROP-2-EN-1-AMINE

CROSS REFERENCE TO RELATED APPLICATIONS

This application claims priority to European application 10191066.9 filed Nov. 12, 2010 and U.S. provisional application 61/413,008 filed Nov. 12, 2010 the contents of which are incorporated herein by reference in their entireties.

BACKGROUND

Field of the Invention

The present invention relates to a process for the preparation of certain 2,2-difluoroethylamine derivatives starting from N-(2,2-difluoroethyl)prop-2-en-1-amine.

2,2-Difluoroethylamine derivatives are useful intermediates in the preparation of agrochemical active substances (see, e.g., WO 2007/115644). Various processes for the preparation of 2,2-difluoroethylamine derivatives are known, e.g. by amide hydrogenation or by reduction with hydrogen.

WO 2009/036900 describes, for example, a process for the preparation of 2,2-difluoroethylamine derivatives by amide hydrogenation of N-[(6-chloropyridin-3-yl)methyl]-2,2-difluoroacetamide (see Scheme 1), which, however, is disadvantageous due to the use of complex hydrides, such as sodium borohydride, since hydrides are very expensive and can only be used with complex safety measures.

Scheme 1:

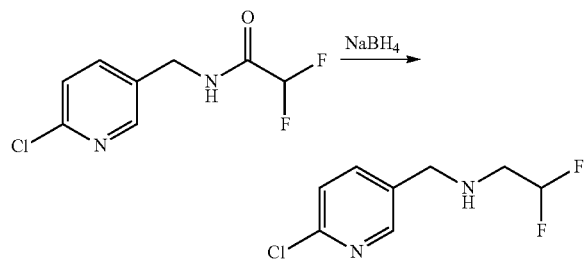

WO 2009/036901 describes the reduction of N-(6-chloropyridin-3-yl)methylene-2,2-difluoroethanamine by hydrogen (see Scheme 2), while WO 2010/105747 describes the reduction of 1-(6-chloropyridin-3-yl)-N-[(1E)-2,2-difluoroethylidene]methanamine by hydrogen. A disadvantage of these processes is the use of hydrogen, because here also the use of hydrogen requires very complex safety measures.

Scheme 2:

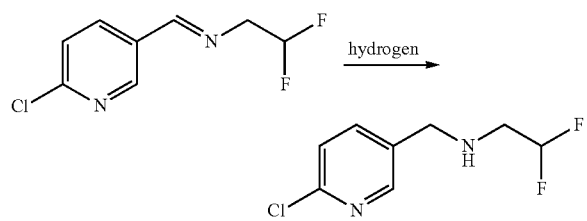

The publication WO2007/115644, which deals with the preparation of insecticidally effective 4-aminobut-2-enolide compounds, describes the preparation of compounds of the general formula A-CH2-NH—R1, in which A is specific heterocycles and R1 is haloalkyl, by alkylation of the nitrogen (Scheme 3).

WO2007/115644 definitely describes the preparation of N-[(6-chloropyridin-3-yl)methyl]-2,2-difluoroethan-1-amine (compound (3)), which is synthesized starting from 2-chloro-5-(chloromethyl)pyridine (compound (2)) and 2,2-difluoroethan-1-amine (compound (1)) in the presence of triethylamine (see Scheme 4). The compounds (1) and (2) and triethylamine are used in this connection in equimolar amounts. The desired product is obtained in a yield of 53%.

Scheme 3:

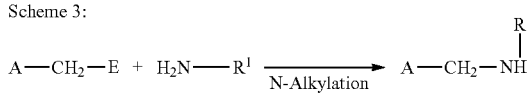

E = Hal, for example chlorine, bromine or iodine; O-toysl, O-mesyl,

Scheme 4:

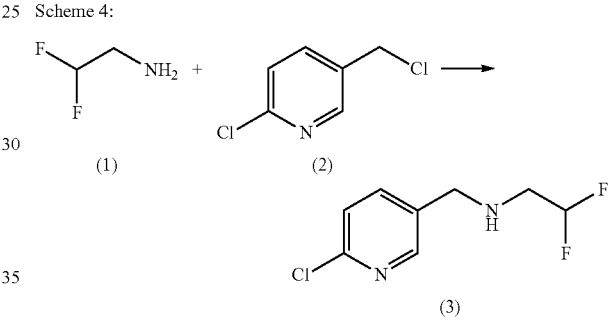

WO 2007/115644 further describes that the compounds N-[(6-chloropyridin-3-yl)methyl]-3-fluoropropan-1-amine and N-[(6-chloropyridin-3-yl)methyl]-2-chloro-2-fluoroethan-1-amine were prepared in the same way.

The process described in WO 2007/116544 for the preparation of compounds of the formula A-CH2-NH—R1, in which A is specific heterocycles and R1 is haloalkyl, is disadvantageous since multiple alkylations of the nitrogen can occur during the reaction. This results in a fall in yield, which can even be recognized in the yield of the example definitely mentioned. The yield was only 53%. These multiple alkylations can only be reduced by the use of a large excess of amine. Apart from the fact that amines are often very cost-intensive, the process is also accordingly uneconomic since the amine added in excess and unreacted has to be either disposed of or recovered, the latter being a complex operation.

Because of the importance of 2,2-difluoroethylamine derivatives as building blocks in the synthesis of agrochemical active substances, it is, however, necessary to find a process which can be used on a commercial scale and inexpensively. It is also worthwhile to obtain the specific 2,2-difluoroethylamine derivatives with high yield and high purity, so that the target compound preferably does not have to be subjected to any additional, possibly complex, purification.

SUMMARY

A simple and accordingly inexpensive process for the preparation of 2,2-difluoroethylamine derivatives of the formula (IV) has now been found, with which the abovementioned disadvantages are avoided.

A subject-matter of the invention is accordingly a process for the preparation of 2,2-difluoroethylamine derivatives of the formula (IV)

which comprises the following steps (i) and (ii):

step (i)—alkylation: reaction of N-(2,2-difluoroethyl)prop-2-en-1-amine of the formula (I)

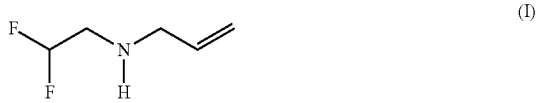

with a compound of the formula (II)

A-CH$_2$-E  (II)

to give a compound of the formula (III)

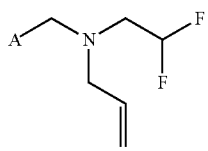

optionally in the presence of an inorganic or organic base, in which, in the formulae (II), (III) and (IV), A is pyrid-2-yl, pyrid-4-yl or pyrid-3-yl, which can optionally be substituted in the 6-position by fluorine, chlorine, bromine, methyl, trifluoromethyl or trifluoromethoxy, or is 1,3-thiazol-5-yl, which can be substituted in the 2-position by chlorine or methyl, or is pyrid-3-yl of the following formula

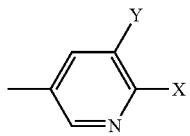

in which

X is halogen, $C_1$-$C_{12}$-alkyl or $C_1$-$C_{12}$-haloalkyl and

Y is halogen, $C_1$-$C_{12}$-alkyl, $C_1$-$C_{12}$-haloalkyl, $C_1$-$C_{12}$-haloalkoxy, azido or cyano, A is preferably 6-fluoropyrid-3-yl, 6-chloropyrid-3-yl, 6-bromopyrid-3-yl, 6-methylpyrid-3-yl, 6-(trifluoromethyl)pyrid-3-yl, 6-(trifluoromethoxy)pyrid-3-yl, 2-chloro-1,3-thiazol-5-yl or 2-methyl-1,3-thiazol-5-yl, 5,6-difluoropyrid-3-yl, 5-chloro-6-fluoropyrid-3-yl, 5-bromo-6-fluoropyrid-3-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5-methyl-6-fluoropyrid-3-yl, 5-methyl-6-chloropyrid-3-yl, 5-methyl-6-bromopyrid-3-yl, 5-difluoromethyl-6-fluoropyrid-3-yl or 5-difluoromethyl-6-chloropyrid-3-yl. A is particularly preferably 6-fluoropyrid-3-yl, 6-chloropyrid-3-yl, 6-bromopyrid-3-yl, 2-chloro-1,3-thiazol-5-yl, 5-fluoro-6-chloropyrid-3-yl, 5,6-dichloropyrid-3-yl, 5-brom-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl or 5-difluoromethyl-6-chloropyrid-3-yl. A is very particularly preferably 6-chloropyrid-3-yl, 6-bromopyrid-3-yl, 2-chloro-1,3-thiazol-5-yl, 5-fluoro-6-chloropyrid-3-yl or 5-fluoro-6-bromopyrid-3-yl, and, in formula (II), E is a leaving group, in particular is halogen (e.g., chlorine, bromine or iodine) or is an activated hydroxyl compound (e.g., mesylate, tosylate or $SO_2CH_3$), E is preferably chlorine, bromine or mesylate, and step (ii): removal of the allyl group (deallylation) from the compound of the formula (III) obtained in step (i), by which a difluoroethylamine derivative of the formula (IV) or a salt thereof is obtained, preferably in the presence of a catalyst and optionally in the presence of a nucleophile.

DETAILED DESCRIPTION OF A PREFERRED EMBODIMENT

The process according to the invention can be illustrated by the following Scheme 5:

Scheme 5:

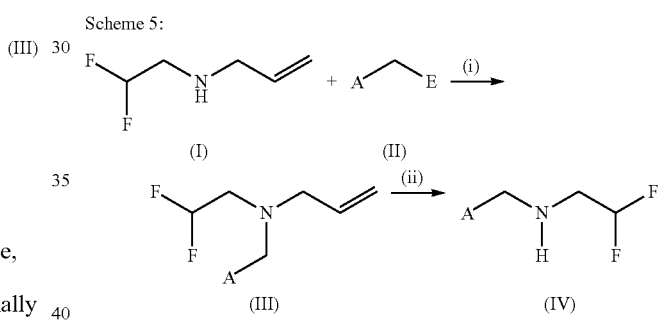

The desired 2,2-difluoroethylamine derivative of the formula (IV) is obtained with the process according to the invention with good yields, with a short reaction time and in high purity, which is why it is generally not necessary to extensively work up the actual reaction product, in particular because the reaction allows only a single alkylation and accordingly prevents the formation of products alkylated several times.

The process according to the invention has, in comparison with the process described in WO2007/115644, the advantage that better yields are achieved and it is accordingly ecologically and economically useful.

A subject-matter of the invention is likewise the process of step (i) for the preparation of a compound of the formula (III)

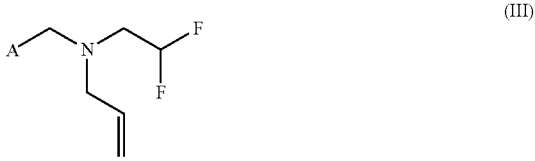

comprising the reaction of N-(2,2-difluoroethyl)prop-2-en-1-amine of the formula (I) with a compound of the formula (II), which comprises the process steps, reaction conditions and reactants described for step (i).

A subject-matter of the invention is likewise the compound of the formula (III)

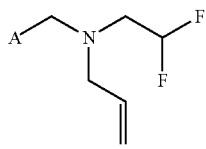
(III)

in which
A is pyrid-2-yl, pyrid-4-yl or pyrid-3-yl, which can optionally be substituted in the 6-position by fluorine, chlorine, bromine, methyl, trifluoromethyl or trifluoromethoxy, or is 1,3-thiazol-5-yl, which can be substituted in the 2-position by chlorine or methyl, or is pyrid-3-yl of the following formula

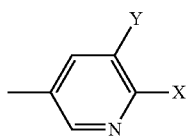

in which
X is halogen, $C_1$-$C_{12}$-alkyl or $C_1$-$C_{12}$-haloalkyl and
Y is halogen, $C_1$-$C_{12}$-alkyl, $C_1$-$C_{12}$-haloalkyl, $C_1$-$C_{12}$-haloalkoxy, azido or cyano,
A is preferably 6-fluoropyrid-3-yl, 6-chloropyrid-3-yl, 6-bromopyrid-3-yl, 6-methylpyrid-3-yl, 6-(trifluoromethyl)pyrid-3-yl, 6-(trifluoromethoxy)pyrid-3-yl, 2-chloro-1,3-thiazol-5-yl or 2-methyl-1,3-thiazol-5-yl, 5,6-difluoropyrid-3-yl, 5-chloro-6-fluoropyrid-3-yl, 5-bromo-6-fluoropyrid-3-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5-methyl-6-fluoropyrid-3-yl, 5-methyl-6-chloropyrid-3-yl, 5-methyl-6-bromopyrid-3-yl, 5-difluoromethyl-6-fluoropyrid-3-yl or 5-difluoromethyl-6-chloropyrid-3-yl. A is particularly preferably 6-fluoropyrid-3-yl, 6-chloropyrid-3-yl, 6-bromopyrid-3-yl, 2-chloro-1,3-thiazol-5-yl, 5-fluoro-6-chloropyrid-3-yl, 5,6-dichloropyrid-3-yl, 5-brom-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl or 5-difluoromethyl-6-chloropyrid-3-yl. A is very particularly preferably 6-chloropyrid-3-yl, 6-bromopyrid-3-yl, 2-chloro-1,3-thiazol-5-yl, 5-fluoro-6-chloropyrid-3-yl or 5-fluoro-6-bromopyrid-3-yl.

A subject-matter of the invention is furthermore the use of the compound of the formula (III)

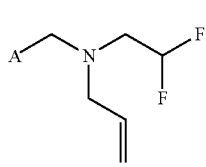
(III)

in the preparation of 2,2-difluoroethylamine, which comprises the process steps, reaction conditions and reactants described for step (ii).

In the context of the present invention, a derivative is understood to mean a derived substance of similar structure to the organic backbone chain (building block) described, i.e. a 2,2-difluoroethylamine derivative is understood to mean in particular a compound which comprises a 2,2-difluoroethylamine building block.

Unless otherwise indicated, the term "alkyl" is understood to mean, either in isolation or, however, in combination with additional terms, such as, for example, haloalkyl, in the context of the present invention, a radical of a saturated, aliphatic hydrocarbon group with from 1 to 12 carbon atoms which can be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, $C_1$-$C_6$-alkyl radicals are particularly preferred. $C_1$-$C_4$-Alkyl radicals are especially preferred.

Unless otherwise indicated, the term "aryl" is understood to mean an aromatic radical with from 6 to 14 carbon atoms, preferably phenyl.

In the context of the present invention, the radicals substituted by halogen, for example haloalkyl, are understood to mean radicals halogenated one or more times up to the maximum possible number of substituents. In the case of radicals which are halogenated more than once, the halogen atoms can be identical or different. Halogen is in this connection fluorine, chlorine, bromine or iodine.

The term "alkoxy", either in isolation or, however, in combination with additional terms, such as, for example, haloalkoxy, is understood to mean in the present case an O-alkyl radical, the term "alkyl" having the above meaning.

Optionally substituted radicals can be substituted one or more times, it being possible for the substituents, in the case of radicals which are substituted more than once, to be identical or different.

Compounds of the formula (I) can be prepared as described in European Patent Application No. 10191059.4 for step (i). In this respect, reference is extensively made to this application.

Compounds of the formula (I) are prepared by the reaction of 2,2-difluoro-1-haloethane of following formula CHF2-CH2Hal, in which Hal is chlorine, bromine or iodine, with prop-2-en-1-amine, preferably in the presence of an organic or inorganic base. The reaction is usually carried out neat, and prop-2-en-1-amine simultaneously acts as acid scavenger. Several preparation processes described in the European Patent Application are again described below.

The compounds of the formula (II) are in some cases known and even commercially available, or can be prepared according to known methods (e.g., the compound 2-chloro-5-chloromethyl-1,3-thiazole, according to DE-A-3 631 538, EP-A-446 913, EP-A-780 384, EP-A-775 700, EP-A-794 180 and WO 97/0010226, the compound 6-chloro-3-(chloromethyl)pyridine, according to DE-A1-3 630 046, EP-A2-373 464, EP-A2-393 453 and EP-A1-569 947, the compound 6-chloro-3-(bromomethyl)pyridine, according to Cabanal-Duvillard, I. et al. (Heterocycl. Commun, 5, 257-262 (1999)), the compounds 6-bromo-3-(chloromethyl)pyridine and 6-bromo-3-(hydroxymethyl)pyridine, according to U.S. Pat. No. 5,420,270 B, the compound 6-fluoro-3-(chloromethyl)pyridine, according to Pesti, J. A. et al. (J. Org. Chem., 65, 7718-7722 (2000)), the compound 6-methyl-3-(chloromethyl)pyridine, according to EP-A2-302389 or according to Van der Eycken, E. et al. (J. Chem. Soc., Perkin Trans (2), 5, 928-937 (2002)), the compound 6-trifluoromethyl-3-(chloromethyl)pyridine, according to WO 2004/082616, or the compound 2-chloro-5-(chloromethyl)pyrazine, according to JP 1993-239034 A2).

General routes for the preparation of compounds of the formula (II) are represented in the following Scheme 6.

Scheme 6:

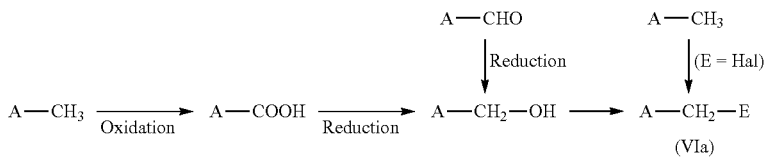

E = Hal, for example chlorine, bromine or iodine; mesylate, tosylate or SO$_2$Me
A = as defined above By way of example, the heterocyclic carboxylic acids (A-COOH) can be converted according to methods known in the literature to the corresponding heterocyclic hydroxymethyl compounds (A-CH2-OH), which subsequently are converted according to methods known in the literature to activated heterocyclic hydroxymethyl compounds (A-CH2-E, E=tosylate or mesylate) or heterocyclic halomethyl compounds (A-CH2-E, E=Hal). The latter can also be obtained from corresponding heterocycles comprising a methyl group (A-CH3) by the use of suitable halogenating agents known in the literature.

The reaction of N-(2,2-difluoroethyl)prop-2-en-1-amine of the formula (I) with A-CH2-E of the formula (II) in step (i) can be carried out neat, i.e. without adding a solvent, or in the presence of a solvent.

In the case of a solvent being added to the reaction mixture in step (i), it is preferably used in such an amount that the reaction mixture remains satisfactorily stirrable during the entire process. Use is advantageously made, based on the volume of the 2,2-difluoro-1-haloethane used, of the solvent in an amount of 1 to 30 times, preferably of 2 to 20 times and particularly preferably of 2 to 15 times. The term solvent is understood to mean, according to the invention, also mixtures of pure solvents. All organic solvents which are inert under the reaction conditions are suitable solvents. Suitable solvents according to the invention are in particular ethers (e.g., ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, 2-methyltetrahydrofuran, dioxane, and ethylene oxide and/or propylene oxide polyethers); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide or diisoamyl sulphoxide; sulphones, such as dimethyl, diethyl, dipropyl, dibutyl, diphenyl, dihexyl, methyl ethyl, ethyl propyl, ethyl isobutyl and pentamethylene sulphone; aliphatic. cycloaliphatic or aromatic hydrocarbons (e.g., pentane, hexane, heptane, octane, nonane, such as white spirits with components with boiling points in the range, for example, from 40° C. to 250° C., cymene, benzine fractions within a boiling point interval from 70° C. to 190° C., cyclohexane, methylcyclohexane, petroleum ether, ligroin, octane, benzene, toluene or xylene); halogenated hydrocarbons, such as dichloromethane, chloroform, carbon tetrachloride, dichloroethane or trichloroethane; halogenated aromatic compounds (e.g., chlorobenzene or dichlorobenzene); amides (e.g., hexamethylphosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine or N,N'-1,4-diformylpiperazine); nitriles (e.g., acetonitrile, propionitrile, n-butyronitrile, isobutyronitrile or benzonitrile); alcohols, such as, e.g., methanol, ethanol, n-propanol, isopropanol, n-butanol, sec-butanol or tert-butanol; ketones (e.g., acetone); or mixtures thereof.

Preferred solvents in step (i) are aromatic and/or aliphatic hydrocarbons, in particular toluene, N,N-dimethylacetamide and N-methylpyrrolidone.

According to the invention, it is preferable to carry out step (i) neat, i.e. without solvent. By doing this, the process can be carried out even more inexpensively as the solvents do not have to be either purchased or disposed of after reaction.

Suitable as leaving group E are groups which exhibit a satisfactory nucleofugicity under the prevailing reaction conditions. Halogens, such as chlorine, bromine or iodine, or mesylate, tosylate or SO2CH3 are in particular suitable leaving groups. Chlorine, bromine and mesylate are preferred leaving groups E.

The reaction in step (i) is advantageously carried out in the presence of a suitable base, such as, for example, an inorganic or organic base.

In step (i), use may in particular be made of one or more of the following inorganic bases: hydrides, hydroxides, amides, alkoxides, acetates, fluorides, phosphates, carbonates and hydrogencarbonates of alkali metals or alkaline earth metals. Preferred bases are sodamide, sodium hydride, lithium diisopropylamide, sodium methoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate and caesium carbonate. The inorganic base is optionally used as an aqueous solution in a concentration in the range from approximately 10 to 40% by weight.

It is likewise possible to use, in step (i), in particular one or more of the following organic bases: tertiary amines, substituted or unsubstituted pyridines and substituted or unsubstituted triethylamine, trimethylamine, N,N-diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2-, 3- or 4-picoline, 2-methyl-5-ethylpyridine, 2,6-lutidine, 2,4,6-collidine, 4-dimethylaminopyridine, quinoline, quinaldine, N,N,N,N-tetramethylethylenediamine, N,N-dimethyl-1,4-diazacyclohexane, N,N-diethyl-1,4-diazacyclohexane, 1,8-bis(dimethylamino) naphthalene, diazabicyclooctane (DABCO), diazabicyclononane (DBN), diazabicycloundecane (DBU), butylimidazole and methylimidazole.

The molar ratio of base to the N-(2,2-difluoroethyl)prop-2-en-1-amine of the formula (I) used lies in the range from approximately 0.1 to approximately 10, preferably in the range from approximately 0.5 to approximately 4 and particularly preferably in the range from approximately 1 to approximately 3. The use of larger amounts of base is possible but is disadvantageous for economic reasons. The base can also simultaneously be solvent.

The molar ratio of the compound of the formula (II) to the N-(2,2-difluoroethyl)prop-2-en-1-amine of the formula (I) used normally lies in the range from approximately 0.5 to approximately 3, preferably in the range from approximately 0.7 to approximately 2 and particularly preferably in the range from 0.8 to approximately 1.5. The use of larger amounts of compound of the formula (II), which is used as alkylating agent, is possible in principle but is disadvantageous economically.

The compound of the formula (II) can be introduced into (added to) the N-(2,2-difluoroethyl)prop-2-en-1-amine of the formula (I) or also in reverse. The compound of the formula (II) and N-(2,2-difluoroethyl)prop-2-en-1-amine of the formula (I) can also be introduced simultaneously.

Although step (i) of the process according to the invention is generally carried out without the addition of a catalyst, catalysts which accelerate the reaction of the compound of the formula (II) with N-(2,2-difluoroethyl)prop-2-en-1-amine of the formula (I) can also be used in the step (i). Mixtures of suitable catalysts are also conceivable.

Examples of suitable catalysts are alkali metal bromides and iodides (e.g., sodium iodide, potassium iodide or potassium bromide); ammonium bromide and ammonium iodide; tetraalkylammonium bromides and iodides (e.g., tetraethylammonium iodide); certain phosphonium halides, such as tetraalkyl- or tetraarylphosphonium halides (e.g., hexadecyl (tributyl)phosphonium bromide, stearyltributylphosphonium bromide, tetrabutylphosphonium bromide, tetraoctylphosphonium bromide, tetraphenylphosphonium chloride and tetraphenylphosphonium bromide), tetrakis(dimethylamino) phosphonium bromide, tetrakis(diethylamino)phosphonium bromide, tetrakis(dipropylamino)phosphonium chloride and bromide; and bis(dimethylamino)[(1,3-dimethylimidazolidin-2-ylidene)amino]methylium bromide.

Of the abovementioned catalysts, sodium iodide, potassium iodide, potassium bromide, tetrabutylammonium bromide or tetraphenylphosphonium bromide are particularly suitable for accelerating the reaction of the step (i). Sodium iodide and potassium iodide may be particularly emphasized.

The catalyst can also be produced in situ, for example by reaction of HBr or HI with ammonia. Furthermore, the catalyst can also be produced in situ by addition of highly reactive alkyl bromides or iodides (e.g., methyl bromide, ethyl bromide, methyl iodide or ethyl iodide).

If the catalyst is present in the step (i), it is used, based on the compound of the formula (II) used, in a concentration of approximately 0.01 to approximately 25% by weight. Higher concentrations are possible in principle. The catalyst is preferably used in a concentration of approximately 0.2 to approximately 25% by weight, particularly preferably of approximately 0.4 to approximately 20% by weight and very particularly preferably of approximately 0.5 to approximately 15% by weight. However, the catalyst can also preferably be used in a concentration of approximately 0.05 to approximately 3% by weight, of approximately 0.1 to approximately 10% by weight or of approximately 0.5 to approximately 10% by weight.

The reaction temperature in step (i) can vary depending on the starting materials used. Step (i) can be carried out at temperatures in the range from approximately −30° C. to approximately 200° C. It is preferable, in carrying out the reaction step (i), for the internal temperature to lie in the range from approximately 10° C. to approximately 150° C., particularly preferably in the range from approximately 25° C. to approximately 130° C.

The reaction time of the reaction in step (i) lies in the range from approximately 0.5 to approximately 20 hours. A longer reaction time is possible but is not useful economically.

The reaction mixture from step (i) is worked up either by filtration and subsequent fractional distillation or by diluting the reaction mixture, subsequent phase separation and subsequent fractional distillation.

The allyl group in the compound of the formula (III) is then again removed (cleaved) in the step (ii). This operation is known as deallylation.

Methods for the cleavage of an allylic C—N bond are known and described, for example in the review by Stephanie Escoubet, Stephane Gastaldi and Michele Bertrand in European Journal of Organic Chemistry (2005), (18), 855-3873. With regard to carrying out the step (ii), reference is made here extensively to these methods. The "Tsuji-Trost reaction" is likewise a deallylation. It is the palladium-catalysed allylation of nucleophiles, such as C-acid compounds, enolates, amines and phenols, with allyl compounds, such as allyl acetates or allyl bromides.

The deallylation can be carried out by isomerization of the double bond of the allyl group to given an enamine, which can then be cleaved by hydrolysis (reaction route (2) in Scheme 7), or the allyl group can transfer to an anionic nucleophile (Nu) and the 2,2-difluoroethylamine be released (reaction route (1) in Scheme 7).

Scheme 7:

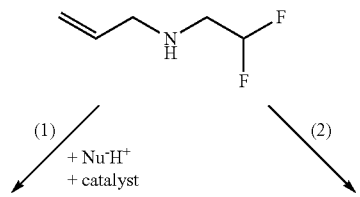

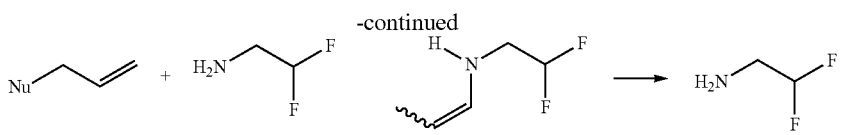

If the deallylation is carried out as represented in Scheme 7 according to reaction route (2), then an acid has to be present in step (ii) for the cleavage of the enamine. Examples of such acids are methanesulphonic acid, p-toluenesulphonic acid, formic acid and acetic acid. The reaction conditions for the cleavage of the allyl group are namely to be so chosen that the 2,2-difluoroethylamine formed is stable; in particular, no strong bases are used for the rearrangement since losses of product otherwise occur. Strong bases are those bases in which the equilibrium reactions are completely on the side of the OH⁻ ions. In a preferred embodiment of the step (ii), the separation of the allyl group from N-(2,2-difluoroethyl)prop-2-en-1-amine takes place in the presence of a suitable catalyst. Suitable catalysts are heterogeneous or homogeneous catalysts which comprise one or more metals from Groups 8-10 of the Periodic Table. The corresponding catalysts can also be used in supported form, for example applied to carbon (charcoal or active charcoal), aluminium oxide, barium sulphate, barium carbonate, silicon dioxide, zirconium dioxide, calcium carbonate or titanium dioxide. Suitable metals are in particular noble metals (e.g., ruthenium, palladium, platinum and rhodium). Palladium(II) chloride, palladium(II) acetate, bis(acetylacetonate)palladium(II), dichlorobis(triphenylphosphine)palladium(II), tetrakis(triethylphosphine)palladium, tetrakis(triphenylphosphine)palladium and ruthenium(III) chloride are suitable as homogeneous catalysts. Preference is given to palladium(0) catalysts, in particular 10% palladium-on-charcoal. Palladium(II) chloride, palladium(II) acetate, bis(acetylacetonate)palladium(II), dichlorobis(triphenylphosphine)palladium(II), tetrakis(triethylphosphine)palladium and tetrakis(triphenylphosphine) palladium are likewise suitable. The catalysts can be used both in their water-moistened form and in their dry form.

If the deallylation of the step (ii) takes place in the presence of a catalyst, then the catalyst is used, based on the compound of the formula (IV) used, in a concentration of approximately 0.001 to approximately 20 mol %. The catalyst is preferably used in a concentration of approximately 0.01 to approximately 10 mol %, particularly preferably of approximately 0.01 to approximately 5.0 mol %.

If the deallylation of the step (ii) takes place in the presence of a catalyst, it is then advantageous for a compound to be present which acts as nucleophile. Typical compounds which act as nucleophiles and accordingly are called nucleophiles are anionic nucleophiles, such as hydroxides, alkoxides, thiolates, carbanions, halides, peroxides, cyanides and azides. The anionic nucleophiles can be used in protonated form. Such protonated nucleophiles are, e.g., thiols, sulphinic acids, 2-mercaptobenzoic acid, malonic acid and the derivatives thereof, and β-dicarbonyl compounds (e.g., barbituric acids, such as N,N'-dimethylbarbituric acid) and amines (e.g., ethanolamine).

It is generally advantageous to carry out step (ii) in the presence of a solvent (diluent) or of solvent mixtures. Solvents are normally used in such an amount that the reaction mixture remains satisfactorily stirrable during the deallylation. All organic solvents which are inert under the reaction conditions are possible as solvent in carrying out step (ii), the type of the solvent used depending on the type of the deallylation.

Mention may be made, as examples, of alcohols, such as methanol, ethanol, isopropanol or butanol; ethers, such as ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, dichlorodiethyl ether, and ethylene oxide and/or propylene oxide polyethers; amines, such as trimethyl-, triethyl-, tripropyl- or tributylamine, N-methylmorpholine, pyridine, alkylated pyridines and tetramethylenediamine; aliphatic, cycloaliphatic or aromatic hydrocarbons, such as pentane, n-hexane, n-heptane, n-octane, nonane and technical-grade hydrocarbons which can be substituted by fluorine and chlorine atoms, such as dichloromethane, trichloromethane, carbon tetrachloride, fluorobenzene, chlorobenzene or dichlorobenzene; cyclohexane, methylcyclohexane, petroleum ether, ligroin, octane, benzene, toluene, bromobenzene, nitrobenzene or xylene; esters, such as methyl, ethyl, butyl or isobutyl acetate, and also dimethyl, dibutyl or ethylene carbonate; water; organic acids, such as formic acid, acetic acid, trifluoroacetic acid or propionic acid, and inorganic acids, such as sulphuric acid, hydrochloric acid or phosphoric acid.

Of the abovementioned solvents, water, ethanol and butanol are preferred.

The reaction mixture after step (ii) can be worked up and the corresponding 2,2-difluoroethylamine derivative of the formula (IV) can be purified, e.g. by distillation or via the corresponding salts (e.g., salts of organic or inorganic acids (e.g., hydrochlorides or acetates)). Normally, the reaction mixture is poured onto water and the pH of the resulting solution is adjusted to 12. The 2,2-difluoroethylamine derivative of the formula (IV) is extracted by extraction with a solvent and is subsequently isolated, preferably by distillation under standard pressure or under vacuum.

The purification of a salt of a 2,2-difluoroethylamine derivative of the formula (IV), for example salts of organic or inorganic acids (e.g., hydrochlorides or acetates), is preferably carried out by crystallization. Water-soluble salts can be purified by extraction of the aqueous solutions, the desired 2,2-difluoroethylamine derivative of the formula (IV) being released by the subsequent reaction with organic or inorganic bases, preferably NaHCO3, Na2CO3 or NaOH.

The present invention is more fully described from the following examples, without the invention being limited thereto.

Preparation of the Starting Compound of the Formula (I) According to European Patent Application No. 10191059.4

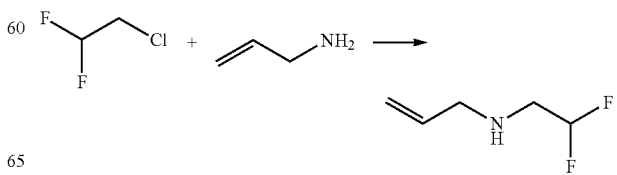

Alternative Form 1:

An amount of 382 g (3.67 mol) of 2,2-difluoro-1-chloroethane and 70 g (1.2 mol) of prop-2-en-1-amine are heated in an autoclave at 120° C. for 16 hours. The reaction mixture is treated with 200 g of water and the phases are subsequently separated. The organic phase is distilled at 55° C. An amount of 65 g of N-(2,2-difluoroethyl)prop-2-en-1-amine is obtained (corresponds to 87.4% yield, based on reacted prop-2-en-1-amine). Unreacted prop-2-en-1-amine, which precipitates as hydrochloride, can be rereleased by addition of sodium hydroxide solution.

$^1$H NMR (CDCl$_3$): 5.76-6.0 (m, 2H), 5.22 (m, 1H), 3.31 (m, 2H), 2.96 (dt, 2H)

Alternative Form 2:

An amount of 382 g (3.67 mol) of 2,2-difluoro-1-chlorethane and 70 g of prop-2-en-1-amine (1.2 mol) are heated in a autoclave at 120° C. for 16 hours. The crude mixture is subsequently filtered and the residue is washed with 150 g of 2,2-difluoro-1-chloroethane. The organic phase is first distilled at standard pressure and 55° C. Residual amounts of 2,2-difluoro-1-chloroethane are removed at 500 mbar and the residue is finely distilled under vacuum. An amount of 56 g of N-(2,2-difluoroethyl)prop-2-en-1-amine is obtained (corresponds to 76% yield). Unreacted prop-2-en-1-amine, which precipitates as hydrochloride, can be rereleased by addition of sodium hydroxide solution.

$^1$H NMR (CDCl$_3$): 5.76-6.0 (m, 2H), 5.22 (m, 1H), 3.31 (m, 2H), 2.96 (dt, 2H)

EXAMPLE 1

According to the Invention—Step (i)

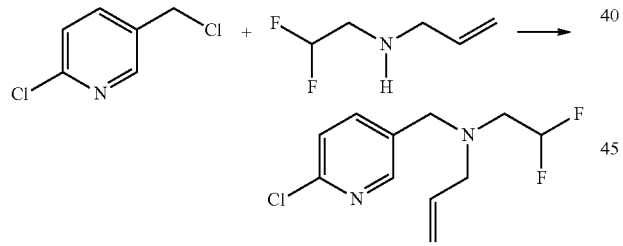

An amount of 16.46 g (0.135 mol) of N-(2,2-difluoroethyl) prop-2-en-1-amine is placed in 31.9 g (0.244 mol) of N,N-diisopropylethylamine and 20 g (0.122 mol) of 2-chloro-5-(chloromethyl)pyridine are introduced at 70° C. The mixture is heated at 70° C. for 16 hours and the excess N,N-diisopropylethylamine is subsequently distilled off. The residue is treated with 100 ml of water and extracted twice with 50 ml of dichloromethane. After drying the combined organic phases over magnesium sulphate, they are filtered through a layer of silica gel and the solvent is removed under vacuum. An amount of 30.3 g (98% content) of N-[(6-chloropyridin-3-yl)methyl]-N-(2,2-difluoroethyl)prop-2-en-1-amine is obtained (corresponds to 97.9% yield).

$^1$H NMR (CDCl$_3$): 8.35 (m, 1H); 7.70 (m, 1H); 7.30 (m, 1H); 5.89-5.78 (tt and m, CF$_2$H and CH); 5.2 (m, 2H); 3.72 (s, 2H); 3.18 (d, 2H), 2.86 (dt, 2H)

EXAMPLE 2

According to the Invention—Step (ii)

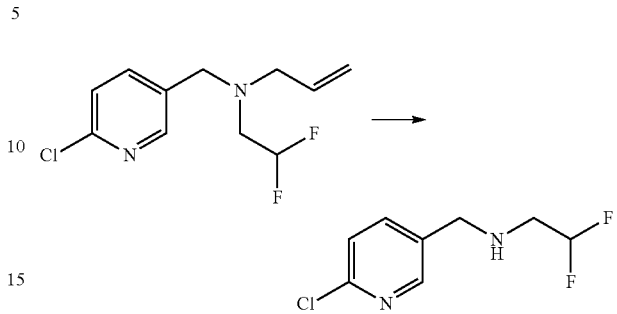

An amount of 2 g (7.38 mmol) of N-[(6-chloropyridin-3-yl)methyl]-N-(2,2-difluoroethyl)prop-2-en-1-amine is placed in 20 ml of n-butanol and treated with 100 mg of 10% palladium-on-charcoal (water-moistened). The mixture is subsequently stirred and heated at reflux for 18 h until complete conversion has been achieved. The reaction mixture is cooled to ambient temperature and then filtered through celite. The solvent is removed under vacuum. An amount of 1.3 g of N-[(6-chloropyridin-3-yl)methyl]-2,2-difluoroethanamine is obtained (corresponds to 84% yield).

$^1$H NMR (CDCl$_3$): 5.5-5.9 (m, 1H), 2.94-3.1 (m, 2H), 1.26 (br m, NH$_2$)

The invention claimed is:

1. A process for the preparation of a 2,2-difluoroethylamine derivative of formula (IV) and/or a salt thereof

(IV)

which comprises the following steps (i) and (ii):

step (i): reaction of N-(2,2-difluoroethyl)prop-2-en-1-amine of formula (I)

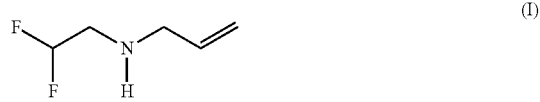

(I)

with a compound of formula (II)

A-CH$_2$-E  (II)

to give a compound of formula (III)

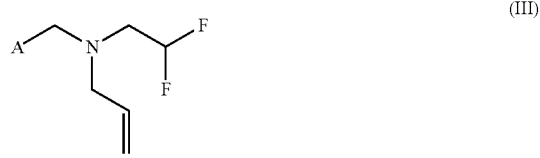

(III)

optionally in the presence of an inorganic or organic base, in which, in the formulae (II), (III) and (IV), A is pyrid-2-yl, pyrid-4-yl or pyrid-3-yl, which can optionally be substituted in the 6-position by fluorine, chlorine, bromine, methyl, trifluoromethyl or trifluoromethoxy, or is 1,3-thiazol-5-yl, which can be substituted in the 2-position by chlorine or methyl, or is pyrid-3-yl of the following formula

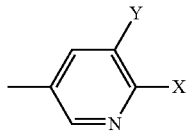

in which

X is halogen, $C_1$-$C_{12}$-alkyl or $C_1$-$C_{12}$-haloalkyl and

Y is halogen, $C_1$-$C_{12}$-alkyl, $C_1$-$C_{12}$-haloalkyl, $C_1$-$C_{12}$-haloalkoxy, azido or cyano, and, in formula (II), E is a leaving group chosen from chlorine, bromine or iodine or an activated hydroxyl compound, mesylate, tosylate and $SO_2CH_3$, and step (ii): removal of the allyl group from the compound of the formula (III) obtained in step (i), by which a difluoroethylamine derivative of the formula (IV) and/or a salt thereof is obtained, optionally in the presence of a catalyst and optionally in the presence of a nucleophile.

2. The process according to claim 1, in which step (ii) is carried out in the presence of a catalyst comprising at least one metal from Groups 8-10 of the Periodic Table of the Chemical Elements and optionally in the presence of a nucleophile, the nucleophile being at least one selected from hydroxides, alkoxides, thiolates, carbanions, halides, peroxides, cyanides and azides, thiols, sulphinic acids, 2-mercaptobenzoic acid, malonic acid and derivatives thereof, and B-dicarbonyl compounds, barbituric acids, N,N'-dimethylbarbituric acid, amines and ethanolamine.

3. The process according to claim 2, in which the catalyst is a palladium catalyst.

4. The process according to claim 3, in which the catalyst is at least one selected from the group consisting of palladium (0) catalysts, 10% palladium-on-charcoal, palladium(II) chloride, palladium(II) acetate, bis(acetylacetonate)palladium(II), dichlorobis(triphenylphosphine)palladium(II), tetrakis(triethylphosphine)palladium and tetrakis(triphenylphosphine)palladium.

5. The Process according to claim 1, in which the inorganic base is at least one selected from the group consisting of hydrides, hydroxides, amides, alkoxides, acetates, fluorides, phosphates, carbonates and hydrogencarbonates of alkali metals or alkaline earth metals, sodamide, sodium hydride, lithium diisopropylamide, sodium methoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate and caesium carbonate, and the organic base is at least one selected from the group consisting of amines, substituted or unsubstituted pyridines and substituted or unsubstituted triethylamine, trimethylamine, N,N-diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2-, 3- or 4-picoline, 2-methyl-5-ethylpyridine, 2,6-lutidine, 2,4,6-collidine, 4-dimethylaminopyridine, quinoline, quinaldine, N,N,N,N-tetramethylethylenediamine, N,N-dimethyl-1,4-diazacyclohexane, N,N-diethyl-1,4-diazacyclohexane, 1,8-bis(dimethylamino)naphthalene, diazabicyclooctane (DABCO), diazabicyclononane (DBN), diazabicycloundecane (DBU), butylimidazole and methylimidazole.

6. The Process according to claim 1, in which, in formula (II), E is chlorine, bromine or mesylate.

7. The Process according to claim 1, in which, in the formulae (II), (III) and (IV), A is 6-fluoropyrid-3-yl, 6-chloropyrid-3-yl, 6-bromopyrid-3-yl, 6-methylpyrid-3-yl, 6-(trifluoromethyl)pyrid-3-yl, 6-(trifluoromethoxy)pyrid-3-yl, 2-chloro-1,3-thiazol-5-yl or 2-methyl-1,3-thiazol-5-yl, 5,6-difluoropyrid-3-yl, 5-chloro-6-fluoropyrid-3-yl, 5-bromo-6-fluoropyrid-3-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5-methyl-6-fluoropyrid-3-yl, 5-methyl-6-chloropyrid-3-yl, 5-methyl-6-bromopyrid-3-yl, 5-difluoromethyl-6-fluoropyrid-3-yl or 5-difluoromethyl-6-chloropyrid-3-yl.

8. The Process according to claim 1, in which, in the formulae (II), (III) and (IV), A is 6-fluoropyrid-3-yl, 6-chloropyrid-3-yl, 6-bromopyrid-3-yl, 2-chloro-1,3-thiazol-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl or 5-difluoromethyl-6-chloropyrid-3-yl.

9. The Process according to claim 1, in which, in the formulae (II), (III) and (IV), A is 6-chloropyrid-3-yl.

10. The Process according to claim 1, in which, in the formulae (II), (III) and (IV), A is 6-bromopyrid-3-yl.

11. The Process according to claim 1, in which, in the formulae (II), (III) and (IV), A is 2-chloro-1,3-thiazol-5-yl.

12. The Process according to claim 1, in which, in the formulae (II), (III) and (IV), A is 5-fluoro-6-chloropyrid-3-yl.

13. The Process according to claim 1, in which, in the formulae (II), (III) and (IV), A is 5-fluoro-6-bromopyrid-3-yl.

14. A compound of formula (III)

in which

A is pyrid-2-yl, pyrid-4-yl or pyrid-3-yl, which can optionally be substituted in the 6-position by fluorine, chlorine, bromine, methyl, trifluoromethyl or trifluoromethoxy, or is 1,3-thiazol-5-yl, which can be substituted in the 2-position by chlorine or methyl, or is pyrid-3-yl of the following formula

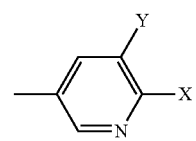

in which
X is halogen, $C_1$-$C_{12}$-alkyl or $C_1$-$C_{12}$-haloalkyl and
Y is halogen, $C_1$-$C_{12}$-alkyl, $C_1$-$C_{12}$-haloalkyl, $C_1$-$C_{12}$-haloalkoxy, azido or cyano.

15. The compound of formula (III),

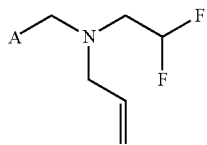

(III)

in which A is 6-fluoropyrid-3-yl, 6-chloropyrid-3-yl, 6-bromopyrid-3-yl, 6-methylpyrid-3-yl, 6-(trifluoromethyl)pyrid-3-yl, 6-(trifluoromethoxy)pyrid-3-yl, 2-chloro-1,3-thiazol-5-yl or 2-methyl-1,3-thiazol-5-yl, 5,6-difluoropyrid-3-yl, 5-chloro-6-fluoropyrid-3-yl, 5-bromo-6-fluoropyrid-3-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5-methyl-6-fluoropyrid-3-yl, 5-methyl-6-chloropyrid-3-yl, 5-methyl-6-bromopyrid-3-yl, 5-difluoromethyl-6-fluoropyrid-3-yl or 5-difluoromethyl-6-chloropyrid-3-yl.

16. The compound of the formula (III) according to claim 14, in which A is 6-chloropyrid-3-yl.

17. The compound of the formula (III) according to claim 14, in which A is 6-bromopyrid-3-yl.

18. The compound of the formula (III) according to claim 14, in which A is 2-chloro-1,3-thiazol-5-yl.

19. The compound of the formula (III) according to claim 14, in which A is 5-fluoro-6-chloropyrid-3-yl.

20. The compound of the formula (III) according to claim 14, in which A is 5-fluoro-6-bromopyrid-3-yl.

* * * * *